(12) United States Patent
Shimada et al.

(10) Patent No.: US 10,130,789 B2
(45) Date of Patent: Nov. 20, 2018

(54) DISTAL ACCESS ASPIRATION GUIDE CATHETER

(75) Inventors: Lynn Shimada, Orange, CA (US); Seferino Torres, Mission Viejo, CA (US); Brian Strauss, Trabuco Canyon, CA (US); Jeffrey Valko, San Clemente, CA (US)

(73) Assignee: Covidien LP, Mansfield, MA (US)

( * ) Notice: Subject to any disclaimer, the term of this patent is extended or adjusted under 35 U.S.C. 154(b) by 1274 days.

(21) Appl. No.: 13/537,246

(22) Filed: Jun. 29, 2012

(65) Prior Publication Data

US 2013/0172851 A1    Jul. 4, 2013

Related U.S. Application Data

(60) Provisional application No. 61/503,546, filed on Jun. 30, 2011.

(51) Int. Cl.
| | | |
|---|---|---|
| *A61M 31/00* | (2006.01) | |
| *A61M 25/00* | (2006.01) | |
| A61M 25/06 | (2006.01) | |
| A61M 25/10 | (2013.01) | |

(52) U.S. Cl.
CPC .... *A61M 25/0043* (2013.01); *A61M 25/0009* (2013.01); *A61M 25/0053* (2013.01); *A61M 25/1002* (2013.01); *A61M 25/0052* (2013.01); *A61M 25/0668* (2013.01); *A61M 2025/1052* (2013.01)

(58) Field of Classification Search
CPC .......... A61M 25/0054; A61M 25/0009; A61M 25/005; A61M 25/0052; A61M 25/0053; A61M 25/0045; A61M 25/00; A61M 25/10; A61M 25/1002; A61M 25/0043; A61M 25/0668; A61B 5/6852; A61L 29/085; A61L 29/00; A51M 25/0053; A51M 25/0009; A51M 25/0052; A51M 25/0043; A51M 25/0062
USPC .............. 604/523–527, 530, 96.01, 264, 508
See application file for complete search history.

(56) References Cited

U.S. PATENT DOCUMENTS

| | | | |
|---|---|---|---|
| 4,676,229 A | | 6/1987 | Krasnicki et al. |
| 4,955,862 A | * | 9/1990 | Sepetka ................... 604/164.13 |

(Continued)

FOREIGN PATENT DOCUMENTS

| | | |
|---|---|---|
| CN | 1258826 A | 7/2000 |
| EP | 523928 A2 * | 1/1993 |

(Continued)

OTHER PUBLICATIONS

International Search Report for PCT/US2012/045184, dated Apr. 10, 2012, 6 pages.

(Continued)

*Primary Examiner* — Kevin C Sirmons
*Assistant Examiner* — Tiffany Legette-Thompson
(74) *Attorney, Agent, or Firm* — Shumaker & Sieffert, P.A.

(57) ABSTRACT

Distal access aspiration guide catheter system and methods for delivering implantable devices, catheters, or substances in or near and/or restoring flow through body lumens, such as blood vessel lumens are described. A distal access aspiration guide catheter having a proximal, medial, and distal possessing high flexibility, high resistance to kinking and a large lumen to wall thickness ratio.

33 Claims, 6 Drawing Sheets

(56) References Cited

U.S. PATENT DOCUMENTS

| | | | |
|---|---|---|---|
| 5,041,100 A * | 8/1991 | Rowland | A61L 29/085 604/264 |
| 5,358,493 A | 10/1994 | Schweich, Jr. et al. | |
| 5,380,304 A | 1/1995 | Parker | |
| 5,405,338 A | 4/1995 | Kranys | |
| 5,454,795 A | 10/1995 | Samson | |
| 5,456,665 A | 10/1995 | Postell et al. | |
| 5,538,512 A | 7/1996 | Zenzon et al. | |
| 5,573,520 A | 11/1996 | Schwartz et al. | |
| 5,658,264 A | 8/1997 | Samson | |
| 5,662,622 A * | 9/1997 | Gore | A61M 25/0012 138/123 |
| 5,695,483 A | 12/1997 | Samson | |
| 5,700,253 A | 12/1997 | Parker | |
| 5,702,373 A | 12/1997 | Samson | |
| 5,728,063 A | 3/1998 | Preissman et al. | |
| 5,730,733 A | 3/1998 | Mortier et al. | |
| 5,795,341 A | 8/1998 | Samson | |
| 5,827,201 A | 10/1998 | Samson et al. | |
| 5,853,400 A | 12/1998 | Samson | |
| 5,876,386 A | 3/1999 | Samson | |
| 5,879,499 A | 3/1999 | Corvi | |
| 6,004,310 A | 12/1999 | Bardsley et al. | |
| 6,022,341 A * | 2/2000 | Lentz | 604/523 |
| 6,022,343 A | 2/2000 | Johnson et al. | |
| 6,036,670 A | 3/2000 | Wijeratne et al. | |
| 6,159,187 A | 12/2000 | Park et al. | |
| 6,171,295 B1 | 1/2001 | Garabedian | |
| 6,186,978 B1 | 2/2001 | Samson et al. | |
| 6,193,705 B1 | 2/2001 | Mortier et al. | |
| 6,213,995 B1 | 4/2001 | Steen et al. | |
| 6,254,588 B1 | 7/2001 | Jones et al. | |
| 6,258,080 B1 * | 7/2001 | Samson | A61M 25/0053 604/525 |
| 6,358,238 B1 | 3/2002 | Sherry | |
| 6,368,315 B1 | 4/2002 | Gillis et al. | |
| 6,368,316 B1 | 4/2002 | Jansen et al. | |
| 6,436,090 B1 | 8/2002 | Sanchez et al. | |
| 6,451,005 B1 | 9/2002 | Saitou et al. | |
| 6,485,457 B1 | 11/2002 | Hisamatsu et al. | |
| 6,503,223 B1 | 1/2003 | Sekido et al. | |
| 6,589,227 B2 | 7/2003 | Sønderskov Klint | |
| 6,616,651 B1 | 9/2003 | Stevens | |
| 6,673,102 B1 * | 1/2004 | Vonesh | A61F 2/07 623/1.13 |
| 6,702,802 B1 | 3/2004 | Hancock et al. | |
| 6,706,025 B2 | 3/2004 | Engelson et al. | |
| 6,808,520 B1 | 10/2004 | Fourkas et al. | |
| 6,991,626 B2 | 1/2006 | Wantink et al. | |
| 7,001,369 B2 | 2/2006 | Griffin et al. | |
| 7,540,865 B2 | 6/2009 | Griffin et al. | |
| 7,704,245 B2 | 4/2010 | Dittman et al. | |
| 7,794,448 B2 | 9/2010 | Grandt et al. | |
| 7,846,148 B2 | 12/2010 | Zhou | |
| 7,850,623 B2 | 12/2010 | Griffin et al. | |
| 7,896,861 B2 | 3/2011 | McFerran et al. | |
| 8,298,210 B2 | 10/2012 | Provost-Tine et al. | |
| 8,926,560 B2 | 1/2015 | Dinh et al. | |
| 2001/0027310 A1 | 10/2001 | Parisi et al. | |
| 2002/0123738 A1 | 9/2002 | Jansen et al. | |
| 2003/0028173 A1 | 2/2003 | Forsberg | |
| 2003/0050686 A1 * | 3/2003 | Raeder-Devens et al. | 623/1.11 |
| 2003/0135198 A1 | 7/2003 | Berhow et al. | |
| 2005/0043713 A1 | 2/2005 | Zhou | |
| 2005/0070879 A1 | 3/2005 | Coyle et al. | |
| 2005/0070881 A1 | 3/2005 | Gribbons et al. | |
| 2005/0234427 A1 | 10/2005 | Eder | |
| 2006/0020256 A1 | 1/2006 | Bell et al. | |
| 2006/0030835 A1 | 2/2006 | Sherman et al. | |
| 2006/0135962 A1 * | 6/2006 | Kick et al. | 606/108 |
| 2006/0135981 A1 * | 6/2006 | Lenker | A61B 17/3439 606/191 |
| 2006/0184106 A1 * | 8/2006 | McDaniel | A61B 18/1492 604/95.04 |
| 2006/0189896 A1 * | 8/2006 | Davis | A61M 25/0013 600/585 |
| 2006/0200074 A1 | 9/2006 | Zadno-Azizi | |
| 2006/0200110 A1 | 9/2006 | Lentz et al. | |
| 2006/0253102 A1 | 9/2006 | Nance et al. | |
| 2006/0229589 A1 | 10/2006 | Itou et al. | |
| 2007/0100285 A1 * | 5/2007 | Griffin | A61M 25/0013 604/164.11 |
| 2007/0135907 A1 * | 6/2007 | Wilson et al. | 623/1.44 |
| 2007/0149951 A1 * | 6/2007 | Wu | A61M 25/09 604/526 |
| 2008/0171952 A1 * | 7/2008 | Mishima | A61M 25/09 600/585 |
| 2008/0188832 A1 | 8/2008 | Tanioka et al. | |
| 2008/0294118 A1 * | 11/2008 | Chandrasekar | A61M 25/02 604/179 |
| 2008/0300577 A1 * | 12/2008 | Trapp | A61L 29/04 604/526 |
| 2009/0024110 A1 * | 1/2009 | Heideman | A61M 25/0012 604/528 |
| 2009/0030373 A1 * | 1/2009 | Gill | A61M 39/0208 604/151 |
| 2009/0166913 A1 | 7/2009 | Guo et al. | |
| 2010/0145267 A1 * | 6/2010 | Bishop | A61B 17/7083 604/96.01 |
| 2011/0004147 A1 * | 1/2011 | Renati | A61B 17/12009 604/9 |
| 2011/0172643 A1 | 7/2011 | Jansen et al. | |
| 2014/0046297 A1 | 2/2014 | Shimada et al. | |

FOREIGN PATENT DOCUMENTS

| | | |
|---|---|---|
| EP | 1010440 A2 | 6/2000 |
| EP | 1092449 A1 | 4/2001 |
| EP | 1123714 A1 | 8/2001 |
| EP | 1955724 | 8/2008 |
| JP | H11506369 A | 6/1999 |
| JP | 11-262529 | 9/1999 |
| JP | 2001129095 A | 5/2001 |
| JP | 2001-508670 | 7/2001 |
| JP | 2001190681 A | 7/2001 |
| JP | 2001218851 A | 8/2001 |
| JP | 2004357779 A | 12/2004 |
| JP | 2005525133 A | 8/2005 |
| JP | 2006288943 A | 10/2006 |
| JP | 2007029736 A | 2/2007 |
| JP | 2008-512196 | 4/2008 |
| JP | 2008188304 A | 8/2008 |
| JP | 2008531213 A | 8/2008 |
| JP | 2011083594 A | 4/2011 |
| JP | 2011514203 A | 5/2011 |
| WO | WO 97/44082 | 11/1997 |
| WO | 0003756 A1 | 1/2000 |
| WO | 03013640 A1 | 2/2003 |
| WO | WO 2006/031582 A2 | 3/2006 |
| WO | 2006094135 A2 | 9/2006 |
| WO | WO 2009/085486 | 7/2009 |
| WO | 2009111505 A1 | 9/2009 |
| WO | 2010068793 A1 | 6/2010 |

OTHER PUBLICATIONS

European Search Report for EP 12 18 5267, dated Feb. 28, 2013, 3 pages.
International Search Report for PCT/US2011/54600, dated Nov. 1, 2013, 3 pages.
Written Opinion of the International Searching Authority for PCT/US2012/045184, 7 pages.
Notice of Reasons for Rejection, and translation thereof, from counterpart Japanese Patent Application No. 2014519215, dated Apr. 27, 2015, 9 pp.
Notice of Reasons for Rejection, and translation thereof, from counterpart Japanese Application No. 2014-519215, dated Dec. 15, 2015, 16 pp.
Third Office Action, and translation thereof, from counterpart Chinese Application No. 201280032625.5, dated Jan. 6, 2016, 9 pp.

(56) References Cited

OTHER PUBLICATIONS

Second Office Action, and translation thereof, from counterpart Chinese Application No. 201280032625.5, dated Aug. 28, 2015, 7 pp.
Notice of Last Preliminary Rejection, and translation thereof, from counterpart Korean Application No. 10-2014-7002176, dated Jan. 29, 2016, 9 pp.
Notification of the First Office Action, and translation thereof, from counterpart Chinese Patent Application No. 201280032625.5, dated Jan. 30, 2015, 14 pp.
Office Action, and translation thereof, from counterpart Russian Application No. 2013155712/14(086902), dated Jul. 26, 2015, 5 pp.
Notice of Preliminary Rejection, and translation thereof, from counterpart Korean Application No. 10-2014-7002176, dated May 29, 2015, 13 pp.
Prosecution History from U.S. Appl. No. 13/878,890, dated May 29, 2013 through Sep. 9, 2016, 45 pp.
The Notification of Allowance from counterpart Japanese Application No. 2014-519215, dated Oct. 19, 2016, 3 pp.
U.S. Department of Health and Human Services, Class II Special Controls Guidance Document for Certain Percutaneous Transluminal Coronary Angioplasty (PTCA) Catheters, Center for Devices and Radiological Health, issued Sep. 8, 2010, 34 pp.
U.S. Department of Health and Human Services, "Guidance for Industry and FDA Staff-Non-Clinical Engineering Tests and Recommended Labeling for Intravascular Stents and Associated Delivery Systems," Center for Devices and Radiological Health, issued Apr. 18, 2010, 56 pp.
Notification of Final Rejection, and translation thereof, from counterpart Korean Application No. 10-2014-7002176, dated Nov. 30, 2016, 5 pp.
Amendment in Response to Office Action dated Sep. 9, 2016, from U.S. Appl. No. 13/878,890, filed Dec. 9, 2016, 17 pp.
Fourth Office Action, and translation thereof, from counterpart Chinese Patent Application No. 201280032625.5, dated Jul. 1, 2016, 7 pp.
The Notification of Reasons for Rejection, and translation thereof, from counterpart Japanese Application No. 2014-519215, dated Jun. 23, 2016, 10 pp.
Notification of Last Preliminary Rejection, and translation thereof, from counterpart Korean Application No. 10-2014-7002176, dated Jul. 27, 2016, 10 pp.
Final Office Action from U.S. Appl. No. 13/878,890, dated Mar. 23, 2017, 14 pp.
Office Action from U.S. Appl. No. 13/878,890, dated Sep. 20, 2017, 13 pp.
International Preliminary Report on Patentability from International Application No. PCT/US2012/045184, dated Jan. 7, 2014, 8 pp.
Examination Report from counterpart European Application No. 12735735.8, dated Jun. 14, 2017, 5 pp.
Prosecution History from U.S. Appl. No. 13/623,941, dated May 9, 2014 through Dec. 5, 2014, 41 pp.
Response to Office Action dated Mar. 23, 2017, from U.S. Appl. No. 13/878,890, filed May 22, 2017, 16 pp.
Advisory Action from U.S. Appl. No. 13/878,890, dated Jun. 21, 2017, 6 pp.
Examination Report from counterpart European Application No. 12735735.8, dated Dec. 21, 2017, 7 pp.
Amendment in response to the Office Action dated Sep. 20, 2017, from U.S. Appl. No. 13/878,890, filed Dec. 7, 2017, 20 pp.
Office Action from U.S. Appl. No. 13/878,890 dated Apr. 19, 2018, 16 pp.
Notice of Intent to Grant and Text Intended to Grant from counterpart European Application No. 12735735.8, dated Jun. 4, 2018, 79 pp.
Amendment in response to Office Action dated Apr. 19, 2018, from U.S. Appl. No. 13/878,890, filed Jul. 12, 2018, 17 pp.

\* cited by examiner

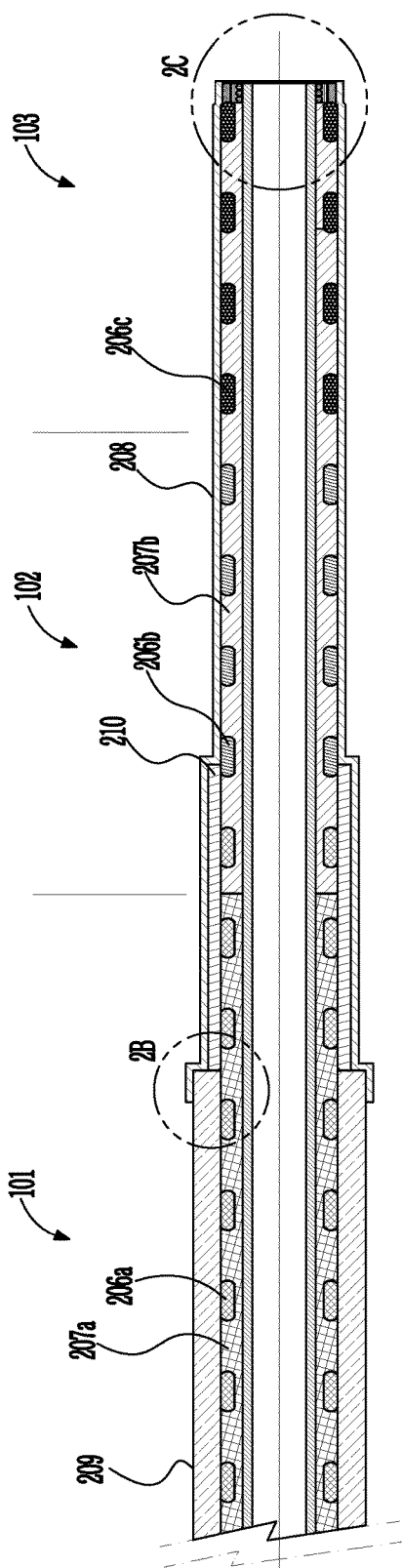
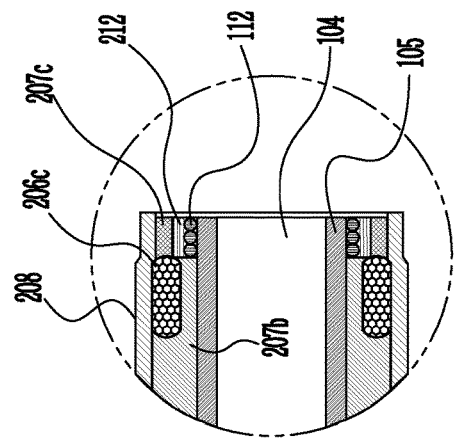
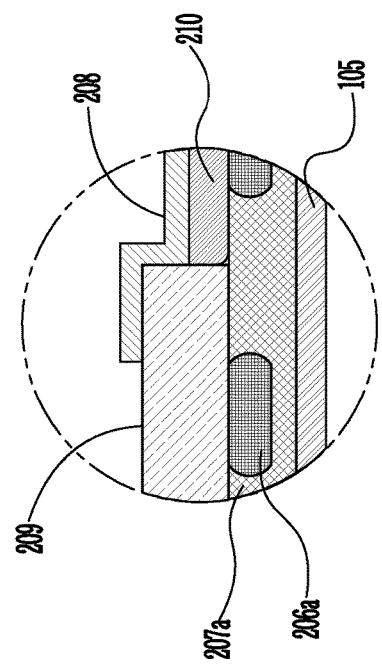
Fig. 2A
Fig. 2C
Fig. 2B

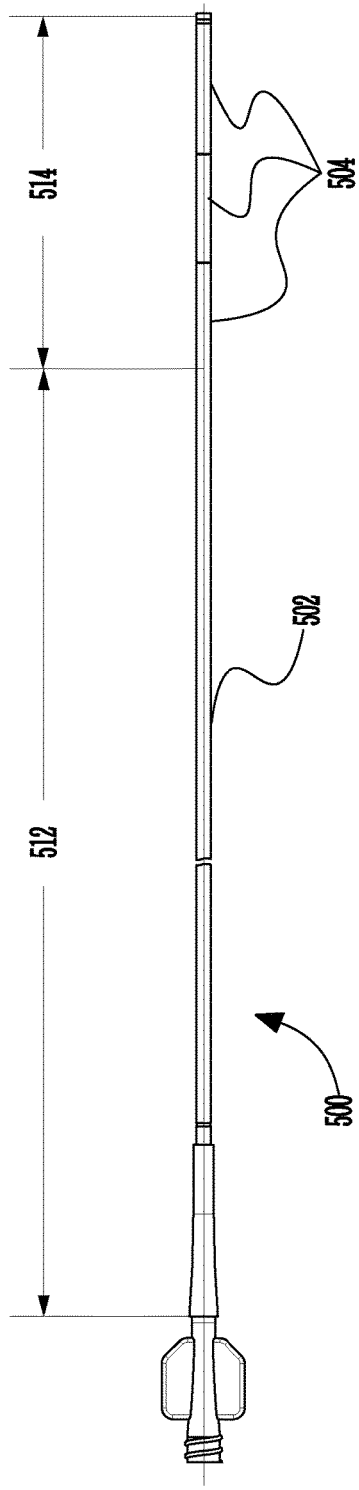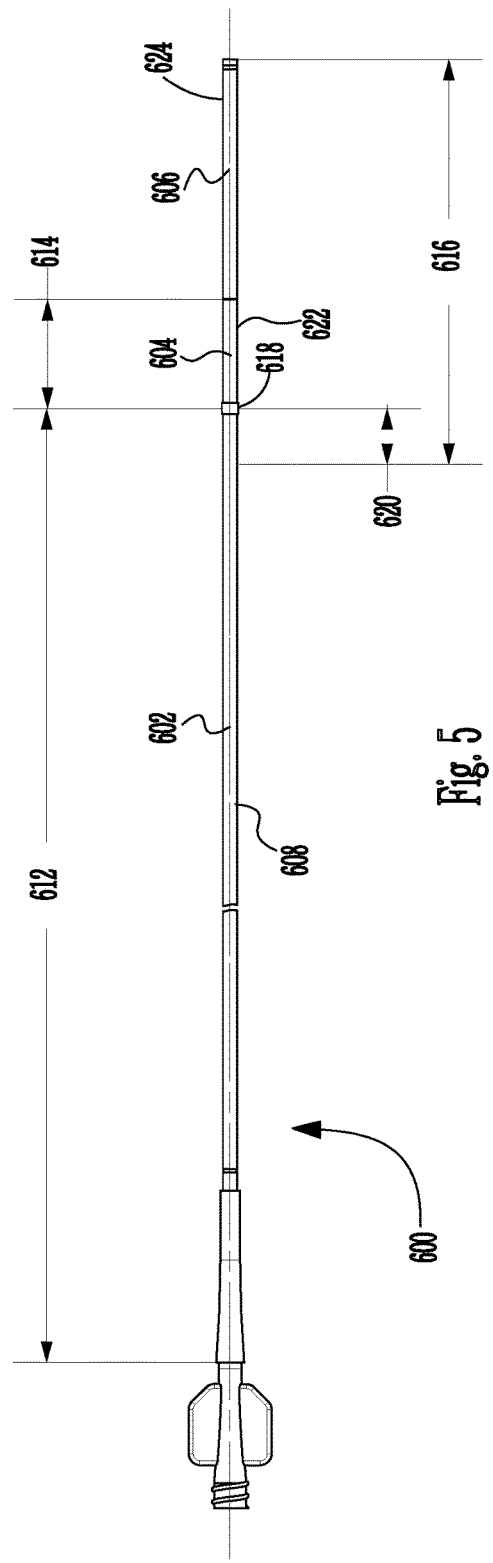

DISTAL ACCESS ASPIRATION GUIDE CATHETER

CROSS REFERENCE TO RELATED APPLICATIONS

The present application claims the benefit of priority to U.S. Provisional Application Ser. No. 61/503,546, filed on Jun. 30, 2011, the entire contents of which are incorporated by reference.

BACKGROUND

1. Technical Field

The present disclosure relates generally to medical devices and methods and more particularly to catheter-based systems and methods useable for accessing, diagnosing, or treating defects in blood vessels, such as blood vessels of the brain.

2. Background of the Related Art

Stroke is a common cause of death and disability. In the United States, approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation (AVM), causing bleeding into the brain tissue and resultant infarction of brain tissue. The remaining 80% of strokes are due to ischemia that occurs due to occlusion of a blood vessel that deprives brain tissue of oxygen-carrying blood. Ischemic strokes are often caused by emboli or pieces of thrombotic tissue that have dislodged and traveled from other body sites, or from the cerebral vessels themselves, to occlude in the narrow cerebral arteries more distally. When a patient presents with neurological symptoms and signs, which resolve completely within 1 hour, the term transient ischemic attack (TIA) is used. Etiologically, TIA, and ischemic stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

To reach these lesions or occlusions microcatheter and microguidewire must be employed, but often the column support of these microcatheters is not strong enough to navigate through the distal reaches of the neurovasculature to effectively treat these sites. Often guide catheters are employed to act as a conduit to help support microcatheter access. Traditional guide catheters designed for coronary or peripheral use (U.S. Pat. Nos. 5,180,376 & 5,484,425 Fischell, U.S. Pat. No. 5,045,072 Castillo, U.S. Pat. No. 5,279,596 Castaneda, U.S. Pat. No. 5,454,795 Samson and U.S. Pat. No. 5,733,400 Gold), typically are not positioned above the skull base and limit their effectiveness in supporting microcatheters in the distal cerebrovasculature. Newer distal access guide catheters have been developed which are slightly longer, thinner, a bit more flexible than the early generations, but are constructed with the same manufacturing techniques as described in U.S. Pat. Nos. 5,180,376 & 5,484,425 Fischell, U.S. Pat. No. 5,045,072 Castillo, U.S. Pat. No. 5,279,596 Castaneda, U.S. Pat. No. 5,454,795 Samson and U.S. Pat. No. 5,733,400 Gold, but have not solved the kinking problem (e.g., Neuron Penumbra Recall—Oct. 2, 2009).

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the terms proximal and distal refer to a direction or a position along a longitudinal axis of a catheter or medical instrument. The term "proximal" refers to the end of the catheter or medical instrument closer to the operator, while the term "distal" refers to the end of the catheter or medical instrument closer to the patient. For example, a first point is proximal to a second point if it is closer to the operator end of the catheter or medical instrument than the second point. The measurement term "French", abbreviated Fr or F, is defined as three times the diameter of a device as measured in mm. Thus, a 3 mm diameter catheter is 9 French in diameter. The term "operator" refers to any medical professional (i.e., doctor, surgeon, nurse, or the like) performing a medical procedure involving the use of aspects of the present disclosure described herein.

In an aspect of the present disclosure, a catheter device for accessing, diagnosing, or treating defects in blood vessels, such as blood vessels of the brain is provided. The catheter device includes a tubular member having an inner lumen and an outer surface that includes a metallic structure having spaces defined therein and a polymeric material disposed within the spaces. An inner liner extends through the lumen of the tubular member and defines an inner lumen of the catheter. There is an outer covering on the outer surface of the tubular member. The polymeric material disposed within the spaces is different from the materials of the inner liner and outer cover.

In another aspect of the present disclosure, a guide catheter section is provided that includes an elongate tubular catheter body having a proximal end and a distal end and a passageway defining an inner lumen extending between those ends. The elongate tubular catheter body includes an inner tubular liner of a first liner material in coaxial relationship with an outer tubular cover and a tubular member between the inner liner and outer cover. The tubular member includes a metallic structure and a polymeric kink resistance member, having the same handedness. The catheter section, in the region of the distal end, has a wall thickness to inner diameter ratio in excess of 16:1 and a lateral flexibility of greater than 1200°/in-lb, and ultimate tensile strength of greater than 15N's In yet another aspect of the present disclosure, a guide catheter includes an elongate tubular member having a proximal end and a distal end and a passageway defining an inner lumen extending between those ends. The elongate tubular member has a relatively stiff proximal segment that includes an inner proximal tubular liner having a proximal liner material in coaxial relationship with an outer proximal tubular cover having a proximal cover material. The proximal segment also includes a metallic braid structure braided upon said inner proximal tubular liner and covered by said outer proximal tubular cover. The elongate tubular member also includes a relatively flexible distal segment. The distal elongate tubular member includes an inner tubular liner of a first liner material in coaxial relationship with an outer tubular cover having a first cover material. The distal elongate tubular member also includes at least a metallic and a polymeric kink resistance member structure having the same handedness and both wound exterior to the inner tubular liner, and covered by said outer tubular cover. The catheter section, in the region of the distal end, having a wall thickness to inner diameter ratio in excess of 16:1 and a lateral flexibility of greater than 1200°/in-lb, and ultimate tensile strength of greater than 15N's. The elongate tubular member also includes at least one intermediate segment defining a passageway between the relatively stiff proximal segment and the relatively flexible distal segment with has a transition from the braided stiffening structure to the metallic and polymeric kink resistance member structure.

In any or all of the aspects described above, the metallic structure may include a nickel titanium alloy such as a nickel titanium alloy ribbon. The metallic structure may be a metal helix having a helical gap where the helical gap is of continuous width or the dimension(s) of the metal helix and/or width of the helical gap varies. Alternatively, the metallic structure may be a metal braid having a number of pics where the number of pics per inch varies.

The polymeric material may be a thermoset polymer, an elastomer, a cast elastomer, or a cast polyurethane. The cast polyurethane may include a thermoset polyurethane adhesive. The inner liner may include at least one material selected from the group consisting of: fluoropolymers; PTFE; PFA and FEP. The outer cover may include at least one material selected from the group consisting of: polyesters and polyolefins.

The catheter device may have a plurality of regions along its length wherein dimension(s) of the metal helix and/or the width of the helical gap differ between said regions. Alternatively, the catheter device may have a plurality of regions along its length wherein dimension(s) the number of pits per inch differ between said regions. Such regions may include a proximal region, a medial region and a distal region.

The outer cover on the proximal region may have a polyester having a thickness of about 0.001 inch, the outer cover on the medial region may have polyester having a thickness of about 0.0005 inch, and the outer over on the distal region may have polyolefin having a thickness of about 0.0005 inch.

The distal region has a lateral flexibility of greater than 1200°/in-lb and a kink radius of about 0.174 inch+/−0.008 inch or less.

In other aspects, the catheter device may also include a balloon where the balloon is a compliant balloon.

In a further aspect of the present disclosure, a method for treating or diagnosing a disorder in a human or animal subject is provided that includes inserting into the subject's vasculature any of the catheter devices described herein. After inserting the catheter device, a substance or device is delivered through the lumen of the catheter device and the substance or device is used to treat or diagnose the disorder.

The catheter may be advanced into a blood vessel located within the subject's skull. The blood vessel into which the catheter device is advanced is selected from the group consisting of: carotid artery, cerebral artery, anterior cerebral artery, middle cerebral artery and posterior cerebral artery.

In yet another aspect of the present disclosure, a method for manufacturing a catheter is provided. The method includes forming or obtaining a metallic structure having spaces defined therein and causing polymeric material to be disposed within the spaces such that the polymeric material and the metallic structure, in combination, form a tubular member having an outer surface and a lumen. An inner liner is disposed within the lumen of the tubular member and an outer cover is disposed on the outer surface of the tubular member.

The inner liner may be disposed on a mandrel and the metallic structure is then positioned on top of the inner liner. The metallic structure may include a nickel titanium alloy disposed about the inner liner and then heat set. A flowable polymer mixture is cast into the spaces and allowed to solidify, thereby forming the tubular member with the inner liner disposed therein. The polymer may be a polymer adhesive such as a thermoset polymer.

A release agent or barrier is applied to one or more selected areas of the metallic structure to deter or interrupt adhesion of the polymer adhesive to the selected areas of the metal helix. The polymer adhesive causes adhesion between the tubular member and the inner liner.

The method also includes causing a quantity of polymer adhesive to be disposed between the outer surface of the tubular member and the inner surface of the outer cover to cause adhesion between the tubular member and the outer cover.

The outer cover comprises a tube that initially has an inner diameter that is larger than the outer diameter of the tubular member and wherein the outer cover is advanced over the tubular member and contacts the tubular member to cause a snug fit on the outer surface of the tubular member. The outer cover is heat shrunk onto the outer surface of the tubular member. A radiographic marker may be disposed on or in the catheter device. In addition, a hydrophilic coating may be applied to an outer surface of the outer cover.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A illustrates a cross-sectional view of the catheter taken along the line 2A-2A of FIG. 1

FIG. 2B illustrates a detailed view of an area outlined in FIG. 2A;

FIG. 2C illustrates a detailed view of an area outlined in FIG. 2A;

FIG. 4 illustrates a side view of a first adhesive layer arrangement of the catheter illustrated in FIG. 1;

FIG. 5 illustrates a side view of a second adhesive layer and cover arrangement of the catheter illustrated in FIG. 1;

DETAILED DESCRIPTION

Figure 1A:
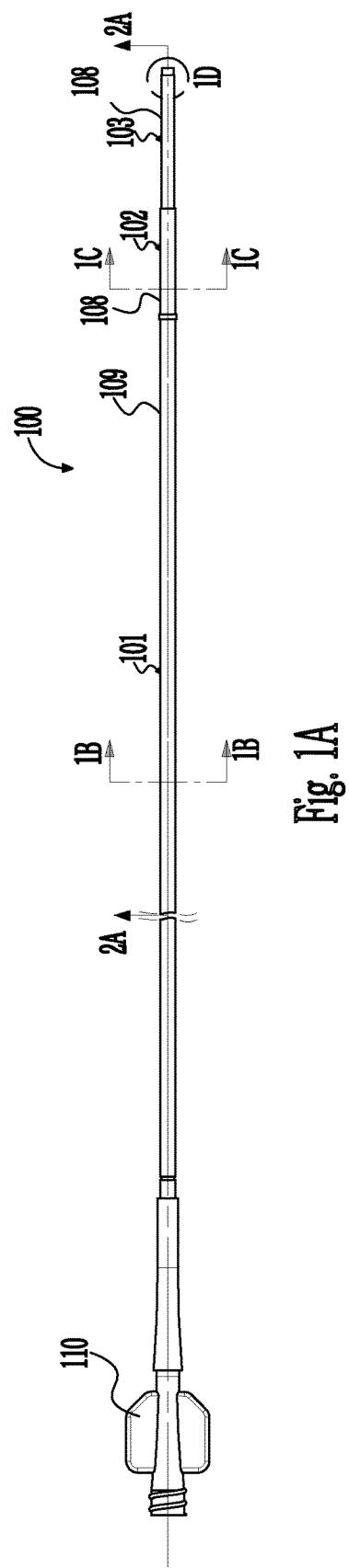
FIG. 1A illustrates a side view of one embodiment of a catheter according to an embodiment of the present disclosure.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

There is provided in accordance with one aspect of the present disclosure, a method for accessing regions of the vasculature through tortuous anatomy. Such vasculature includes the cerebrovasculature wherein access to the Circle of Willis and beyond is exceedingly difficult due to the carotid siphon or vertebral artery anatomy that must be traversed to reach such locations without undo trauma or vessel straightening. The method comprises the steps of providing a catheter having a proximal end and a distal end. The distal end of the catheter is inserted into the artery, and the support is distally advanced. Negative pressure can be applied to the proximal end of the catheter, or an affixed aspiration port, to draw the thromboembolic material into the distal section. Catheters and other instrumentation (working devices) can be inserted through the distal access aspiration guide catheter within the vasculature to gain access to locations where flexibility, kink resistance, torqueability, and column strength are required.

Typical arteries may be, among other examples, the common carotid artery, the internal carotid artery, the carotid siphon, the Circle of Willis, etc. Alternatively, the artery may be the middle cerebral artery or the anterior cerebral artery, or elsewhere in the brain.

The method may additionally comprise the steps of introducing oxygenated medium into the artery through the aspiration lumen, or infusing pharmaceutical agent into the artery through the aspiration lumen. The pharmaceutical agent may be a vasodilator such as nifedipine or nitroprusside. The pharmaceutical agent may alternatively comprise t-PA. The thromboembolic material may be located using intravascular ultrasound, or carotid Doppler imaging techniques.

In accordance with another aspect of the present disclosure, there is provided an intracranial aspiration catheter. In accordance with the present disclosure, there is provided a method of establishing a flow path through a catheter, positioned across a non-linear segment of vasculature.

In certain embodiments, the aspiration catheter can serve as a guide catheter for placement of the micro-catheter. The guide catheter is advanced to a target region in cooperation with a guidewire to allow for steering and manipulation through the vasculature. In an exemplary procedure, the guidewire and guide catheter are introduced into the vasculature at a site within a femoral or iliac artery. Using a Seldinger technique, or other percutaneous procedure, a hollow 18-Gauge needle can be introduced into a femoral artery via percutaneous procedure. A guidewire is next advanced through the hollow needle and into the arterial tree. The hollow needle is next removed and an introducer sheath is advanced into the arterial tree. The guide catheter is next advanced through the catheter introducer either through the same guidewire or through a larger guidewire suitable for aortic traverse. The guide catheter is advanced through the aortic arch, into a carotid artery, through the carotid siphon and into a region proximate the circle of Willis. The guide catheter, because of its flexibility and high kink resistance can easily inserted through tortuous anatomy beyond the carotid siphon or the vertebral and basilar arteries. Once properly placed, the guide catheter can be utilized as a large conduit for the insertion of other working devices. Because of its large inner diameter multiple devices can be inserted. The guide catheter can serve as an aspiration device and as a shield for retrieval of debris, thrombus, or other material from the vasculature.

The guide catheter is terminated, at its proximal end, with a luer or hemostasis valve and optionally with a connector offering multiple access ports, each of which can be valved or be terminated with a stopcock, etc.

There is disclosed a distal access aspiration catheter 100 in accordance with one aspect of the present disclosure. Although primarily described in the context of distal access aspiration guide catheter with a single central lumen, catheters of the present disclosure can readily be modified to incorporate additional structures, such as permanent or removable column strength enhancing mandrels, two or more lumens to permit drug or irrigant infusion or radiation delivery or to supply inflation media to an inflatable balloon, or combinations of these features, as will be readily apparent to one of skill in the art in view of the disclosure herein. Further, catheters of the present disclosure may have a rapid exchange configuration. In addition, the present disclosure will be described primarily in the context of providing distal vascular access for other endovascular working devices and removing obstructive material from remote vasculature in the brain.

The catheters disclosed herein may readily be adapted for use throughout the body wherever it may be desirable to introduce a very flexible thin walled catheter and kink resistant, which provides a relatively large diameter aspiration or supported working channel. For example, catheter shafts in accordance with the present disclosure may be dimensioned for use throughout the coronary and peripheral vasculature, the gastrointestinal tract, the urethra, ureters, Fallopian tubes and other lumens and potential lumens, as well. The lumen structure of the present disclosure may also be used as a minimally invasive percutaneous tissue tract expander, such as for diagnostic or therapeutic access to a solid tissue target (e.g., breast biopsy or tissue excision).

Figure 1D:
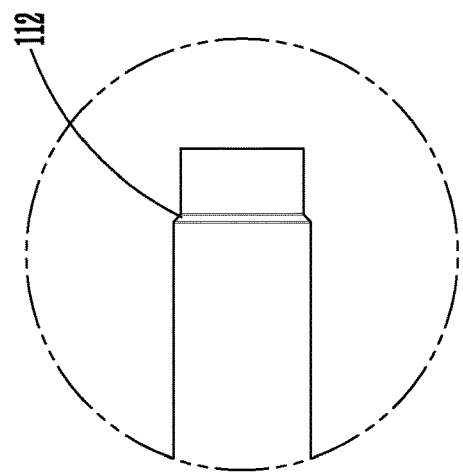
FIG. 1D illustrates a detailed view of the area outlined in FIG. 1.
Figure 1C:
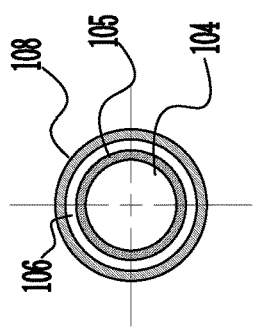
FIG. 1C illustrates a cross-sectional view of the catheter taken along the line 1C-1C of FIG. 1.
Figure 1B:
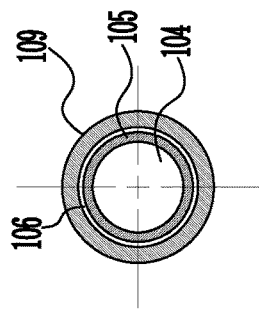
FIG. 1B illustrates a cross-sectional view of the catheter taken along the line 1B-1B of FIG. 1.

FIGS. 1A-1D illustrate a guide catheter 100 according to an embodiment of the present disclosure. In this example, the guide catheter 100 comprises an elongate body having a proximal section 101, a medial section 102 and a distal section 103. A lumen 104 extends through the catheter 100. The elongate body of the catheter comprises an inner liner or sleeve 105, and a kink resistant member 106. A distal outer cover 108 is disposed on the distal section 103 and medial section 102 and a proximal tubular cover 109 is disposed on the proximal section 101. A luer or manifold 110 is provided on the proximal end of the elongate catheter body. Optionally, one or more radiographic marker(s) 112 may be positioned on or in the elongate catheter body, such as at the distal tip as shown in the example of FIGS. 1A and 1D.

The polymers comprising the proximal tubular cover 109 and the distal tubular cover 109 are heat set using heat shrink tubing or other compression methodology and heat, such as that generated by a heated air flow source, radiant heat source, induction heater, radiofrequency heater, or the like. Alternatively, the proximal tubular cover 109 and the distal tubular cover 109 may be set by overcoating the catheter by extrusion, dip coating, spray coating, vapor deposition, etc.

Figure 3A:
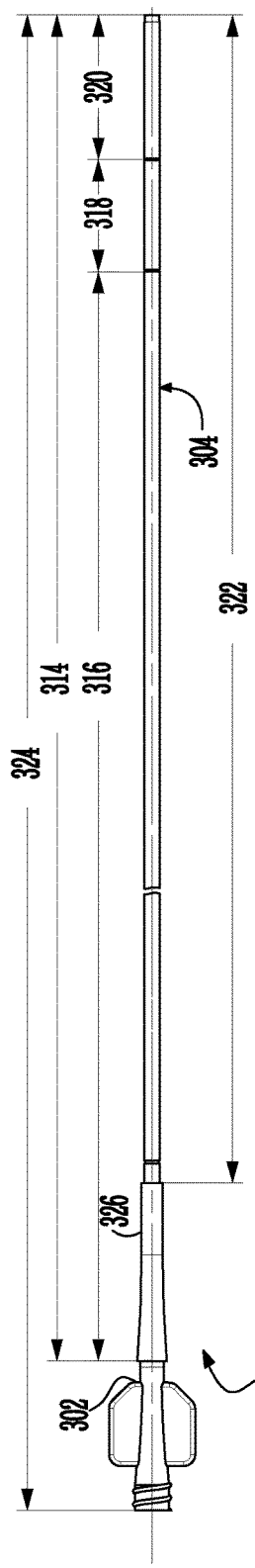
FIG. 3A illustrates a side view of a liner and reinforcement layer assembly of the catheter illustrated in FIG. 1.
Figure 3B:
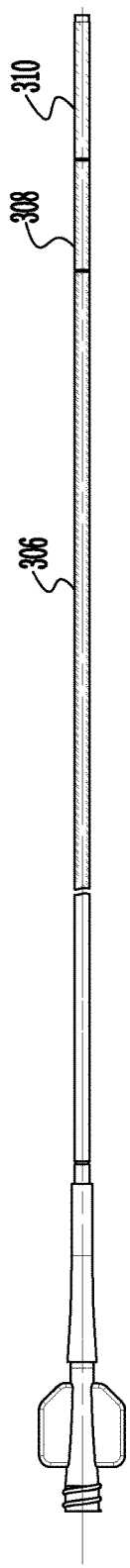
FIG. 3B illustrates a side view of the proximal, medial, and distal coils according to an embodiment of the present disclosure.
Figure 3C:
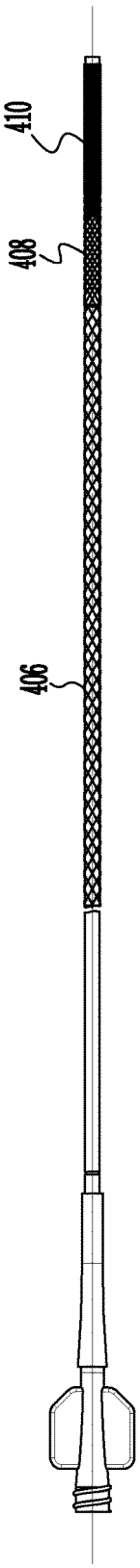
FIG. 3C illustrates a side view of the proximal, medial, and distal braids according to another embodiment of the present disclosure.

The kink resistant member 106 includes metallic structures 206a, 206b, 206c (FIG. 2A) in the form of helical coil (FIG. 3B) or braid (FIG. 3C). With a helical coil, the winds (i.e., helical convolutions) of metallic structures 206a, 206b, 206c are disposed such that distributed flexibility can be generated along the lengths of the catheter shaft. With a braid, the pics are disposed such that distributed flexibility can be generated along the lengths of the catheter shaft. The metal used in metallic structures 206a, 206b, 206c can be nitinol, stainless steel, cobalt-nickel alloy, titanium, or the like. Metallic structures 206a, 206b, 206c may be faulted by winding one or more wires to form a helical coil or a braid. The wires may have a flat-wire cross-section, a circular cross-section, or any other polygonal cross-section. Alternatively, in other embodiments, metallic structures 206a, 206b, 206c may be formed from a metallic tube that is laser cut, chemically etched, or grinded to form a desired pattern for metallic structures 206a, 206b, 206c. In another embodiment, metallic structures 206a, 206b, 206c may be built upon a removable substrate by electrodeposition, vapor deposition, sintering, or any other processes that may be used to build metallic structures 206a, 206b, 206c on a removable substrate.

The gap within the metallic winds of the helical coil or pics in the braid are filled with polymeric kink resistant members 207a and 207b, which can cause the flexibility to be substantially evenly distributed, or directed along a specific axis. The polymeric kink resistant member 207 may be a thermoset polymer (e.g., thermoset urethane), thermoplastic, or the like. Additionally, polymeric kink resistant members 207a and 207b may be a polymer that is firmed up by solvent evaporation, cross linking, or a room-temperature vulcanized (RTV) polymer. Moreover, metallic structures 206a, 206b, 206c may be overcoated by extrusion, dip coated, spray coated, vapor deposition, etc.

The kink resistant member 106 can beneficially be created such that the reinforcement becomes more flexible moving distally by changing the gap or thicknesses of metallic structures 206a, 206b, 206c and/or polymeric kink resistant members 207a and 207b. Additionally the flexibility can also be adjusted be changing the thicknesses and materials of the inner sleeve 105 and/or outer tubular covers 108 and/or 109.

The proximal end of the catheter is additionally provided with luer or a manifold 110 having one or more access ports as is known in the art. Generally, the manifold is provided with a guidewire port in an over-the-wire construction, an aspiration port, and a catheter insertion port. One or more of these features can be embodied within a single port. Alternatively, the aspiration port may be omitted if the procedure involves removal of the guidewire proximally from the guidewire port following placement of the aspiration catheter, and aspiration through the guidewire port. Additional access ports may be provided as needed, depending upon the functional capabilities of the catheter. The manifold may be injection molded from any of a variety of medical grade plastics, or formed in accordance with other techniques known in the art.

The proximal body segment will exhibit sufficient column strength to permit axial positioning of the catheter through a patient's vasculature. The catheter body may further comprise other components, such as radiopaque fillers; colorants; reinforcing materials; reinforcement layers, such as braids and helical reinforcement elements; or the like. In particular, the proximal body segment may be reinforced in order to enhance its column strength and torqueability while limiting its wall thickness and outside diameter.

When present, an optional radiographic marker 112 will typically be provided at least at the distal end of the catheter 100. Other radiopaque markers may be provided elsewhere, such as on the support coil, if it is not already radiopaque. One embodiment of a radiopaque marker that may be used comprises a metal band, which is fully recessed within the distal end of the proximal body segment. Suitable marker bands can be produced from a variety of materials, including platinum, gold, and tungsten/rhenium alloy. The radiopaque metal band may be recessed in an annular channel formed at the distal end of the proximal body segment.

Diameters outside of the preferred ranges may also be used, provided that the functional consequences of the diameter are acceptable for the intended purpose of the catheter. For example, the lower limit of the diameter for any portion of tubular body in a given application will be a function of the number of fluid or other functional lumen contained in the catheter, together with the acceptable minimum aspiration flow rate and collapse resistance.

Tubular catheter body must have sufficient structural integrity (e.g., column strength or "pushability") to permit the catheter to be advanced to distal locations without buckling or undesirable bending of the tubular body. The ability of the body to transmit torque may also be desirable, such as to avoid kinking upon rotation, to assist in steering. The tubular catheter body, and particularly the distal section, may be provided with any of a variety of torque and/or column strength enhancing structures. For example, axially extending stiffening wires, spiral wrapped support layers, braid(s) or woven reinforcement filaments may be built into or layered on all or part of the tubular catheter body.

In many applications, the proximal section will not be required to traverse particularly low profile or tortuous arteries. For coronary vascular applications, for example, the proximal section will be mostly or entirely within the relatively large diameter guide catheter. The transition can be located on the catheter shaft to correspond approximately with the distal end of the guide catheter when the balloon and/or distal end is/are at the treatment site. For certain other applications, such as intracranial catheterizations, the distal section is at least about 5 cm long and small enough in diameter to pass through vessels as small as 3 mm or 2 mm or smaller. Catheters for this application may have a proximal section length of between about 60 cm to about 150 cm and a distal section length of between about 5 cm to about 15 cm, and the distal section is able to track a tortuous path of at least about 5 cm through vessels of less than about 3 mm lumen ID.

The number of catheter body sections may vary. For example, distal section 103 may comprise a first distal section and a second distal section. The dimensions (e.g., width, thickness) of the metal structure 206 and/or the outer cover 108 may vary between the two distal sections, thereby causing them to have different properties.

Table 1 below shows examples of inner diameter to wall thickness ratios for catheters of the present disclosure in sizes ranging from 4 French to 8 French. In some embodiments, the inside diameter (ID) to wall thickness or wall section can include ratios from about 16:1 to about 24:1.

| Catheter Size | Wall Thickness | Preferred Wall Thickness | Inside Diameter (ID) |
|---|---|---|---|
| 8 French | 0.0045"-0.0055" | 0.005" | 0.094"-0.096" |
| 7 French | 0.004"-0.005" | 0.0045" | 0.082"-0.084" |
| 6 French | 0.003"-0.004" | 0.0035" | 0.072"-0.073" |
| 5 French | 0.003"-0.0035" | 0.00325" | 0.059"-0.060" |
| 4 French | 0.0025"-0.003" | 0.00275" | 0.046"-0.047" |

In an 8 French catheter, the wall thickness can range from about 0.0045 to 0.0055 inches, with a preferred wall thickness of about 0.005 inches and the inside diameter of the catheter can preferably range from about 0.094 inches to about 0.096 inches.

In a 7 French catheter, the wall thickness can range from about 0.004 to 0.005 inches, with a preferred wall thickness of about 0.0045 inches and the inside diameter of the catheter can preferably range from about 0.082 inches to about 0.084 inches.

In a 6 French catheter, the wall thickness can range from about 0.003 to 0.004 inches, with a preferred wall thickness of about 0.0035 inches and the inside diameter of the catheter can preferably range from about 0.072 inches to about 0.073 inches.

In a 5 French catheter, the wall thickness can range from about 0.003 to 0.0035 inches, with a preferred wall thickness of about 0.00325 inches and the inside diameter of the catheter can preferably range from about 0.059 inches to about 0.060 inches.

In a 4 French catheter, the wall thickness can range from about 0.0025 to 0.003 inches, with a preferred wall thickness of about 0.00275 inches and the inside diameter of the catheter can preferably range from about 0.046 inches to about 0.047 inches.

FIGS. 2A-2C illustrate cross-sectional views of a catheter 100 in accordance with an embodiment of the present disclosure. As shown in FIGS. 2A-2C, a lumen 104 is defined by inner line 105. Metallic structure 206a is disposed on the inner line 105 in proximal section 101, metallic structure 206b is disposed on the inner liner 105 in medial section 102, and metallic structure 206c is disposed on the inner liner 105 in distal section 103. Metallic structures 206a, 206b, and 206c may be composed of a single wire or multiple wires. A first polymeric kink resistant member 207a is disposed between the spaces in metallic structure 206a while a second polymeric kink resistant member 207b is disposed between the spaces in metallic structures 206b and 206c. An adhesive 207c is disposed over the radiographic marker 112 to form a tip. A polymeric layer 210 is also disposed over the distal end of metallic structure 206a. The outer cover of the catheter 100 includes a proximal tubular cover 209 disposed in proximal section 101. The outer cover also includes a distal outer cover 208 that is disposed over distal section 103, medial section 102 and a portion of proximal section 101.

FIGS. 3A-3C illustrates a side view of an aspiration guide catheter subassembly 300 comprising a hub 302 and an inner liner 304. FIG. 3B illustrates a plurality of coil windings 306, 308, 310, detailing the catheter liner and coil subassembly arrangement. FIG. 3C illustrates a plurality of braided sections 406, 408, 410. The subassembly 300 further comprises a strain relief 326, an overall length 324, a working length 322, a PTFE liner length 314, a distal section length 320, a medial section length 318, and a proximal section length 316.

Referring to FIG. 3A, the inner liner 304 can comprise PTFE, PFA, FEP, or other lubricious polymer. The exterior diameter surface of the inner liner 304 can be etched to increase its roughness. Such etching can be performed using methodology including, but not limited to, plasma discharge treatment, mechanical abrasion, laser etching, and the like. The inner liner 304 is generally disposed over a removable mandrel of the appropriate diameter, said mandrel (not shown) comprising a metallic core and an exterior lubricious coating such as PTFE, FEP, PFA, Parylene, or the like. The hub 302 can be fabricated from a variety of polymers selected from materials including, but not limited to, polyethylene, polypropylene, acrylonitrile butadiene styrene (ABS), polysulfone, polycarbonate, polyvinyl chloride, polystyrene, polyester, and the like. The hub 302 can also be fabricated from metals such as, but not limited to, stainless steel, titanium, cobalt nickel alloy, and the like. The hub 302 comprises a through lumen (not shown) that can slidably accept devices up to the indicated size of the guide catheter subassembly 300, namely about 4, 5, 6, 7, 8, and 9 French, for example. The hub 302 can comprise a strain relief in the region where it is affixed to the tubing of the guide catheter subassembly 300 to minimize kinking and transfer forces to the guide catheter subassembly 600 under maximum control. Attachment between the hub 302 and other components of the subassembly 300 can comprise ultraviolet (UV) light curing adhesive such as, but not limited to, Dymax™ 1128-M-VT UV curing adhesive, or the like. The attachment between the hub 302 and the other components of the catheter subassembly 300 can also comprise cyanoacrylate adhesive such as, but not limited to, Loctite 4011, and the like.

Referring to FIG. 3B, the spacing on the distal coil 310 can be approximately 0.008, with a range of about 0.006 to 0.010 inches. The spacing on the medial coil 308 can be approximately 0.004 inches with a range of about 0.002 to 0.006 inches. The spacing on the proximal coil 306 can be approximately 0.001 inches with a range of about 0.0005 to 0.002 inches. The tighter the spacing of the coils 306, 308, 310 the stiffer the system and the greater the torque carrying capability of the system. Thus, the proximal coil 306 is stiffer than the medial coil 308, which is, in turn, stiffer than the distal coil 310. The coils 306, 308, 310 can be fabricated from nitinol with superelastic or pseudoelastic properties.

The width of the individual turns in the coil can range in width from about 0.001 inches to about 0.010 inches and the thickness of the individual turns in the coil can range from about 0.0005 to about 0.005 inches. The coils 306, 308, 310 may have spring characteristics and is not malleable. The coils 306, 308, 310 can be fabricated from nitinol, as previously stated, but it can also be fabricated from materials such as, but not limited to, cobalt nickel alloy, titanium, stainless steel, polyester, polyethylene naphthalate, and the like.

Referring to FIG. 3C, the pics per inch (PPI) on the distal braid 410 can be approximately 20-50 PPI. The PPI on the medial braid 408 can be approximately 50-100 PPI. The PPI on the proximal braid 406 can be approximately 100-150 PPI. The smaller the PPI of the braids 406, 408, 410 the stiffer the system and the greater the torque carrying capability of the system. Thus, the proximal braid 406 is stiffer than the medial braid 408, which is, in turn, stiffer than the distal braid 410. The braids 406, 408, 410 can be fabricated from nitinol with superelastic or pseudoelastic properties. The thickness of the braid strands can range in width from about 0.001 inches to about 0.010 inches and the thickness of the braid strands can range from about 0.0005 to about 0.005 inches. The braids 406, 408, 410 may have spring characteristics and is not malleable. The braids 406, 408, 410 can be fabricated from nitinol, as previously stated, but it can also be fabricated from materials such as, but not limited to, cobalt nickel alloy, titanium, stainless steel, polyester, polyethylene naphthalate, and the like.

Although, FIG. 3B describes the use of different coils in the proximal, medial, and distal sections of the guidewire and FIG. 3C describes the use of different braids in the proximal, medial, and distal sections of the guidewire, in some embodiments, different combinations of coils and braids can be used in the various sections to improve the torque and flexibility of the guidewire.

The liner and coil subassembly 300 construction for a catheter having a working length 322 (catheter length exclusive of the hub, strain relief 326 or any other attachments) of 105-cm is as follows: The overall length 324 can be about 113-cm, the working or usable length 322 can be about 105-cm, the liner length 314 can be about 110-cm, the proximal coil length 316 can be about 96-cm, the medial coil length 318 can be about 6-cm, and the distal coil length 320 can be about 8-cm.

The liner and coil subassembly 300 construction for a catheter having a working length 322 of 115-cm is as follows: The overall length 324 can be about 123-cm, the working or usable length 322 can be about 115-cm, the liner length 314 can be about 120-cm, the proximal coil length 316 can be about 106-cm, the medial coil length 318 can be about 6-cm, and the distal coil length 320 can be about 8-cm.

FIG. 4 illustrates a side view of an aspiration guide catheter subassembly 500 comprising a plurality of first adhesive layers 502, 504 disposed over and between the coils 306, 308, 310 or braids 406, 408, 410 of the aspiration guide catheter subassembly 300.

Referring to FIG. 4, the first adhesive layer 502, disposed over the proximal regions of the subassembly 500, comprises materials such as, but not limited to, Flexobond 431™, supplied by Bacon Co., Irvine, Calif. The distal first adhesive layer 504, disposed over the distal regions of the subassembly 500, comprises materials such as, but not limited to, Flexobond 430™, supplied by Bacon Co., Irvine, Calif. The proximal first adhesive layer 502 can be configured to provide increased stiffness relative to that of the distal first adhesive layer 504. The first adhesive layers 502, 504 generally are applied to the subassembly 500 along the entire length of the tubing 314 and the thickness of the layers 502, 504 is approximately equal to, or slightly greater than that of the coils 306, 308, 310 or braids 406, 408, 410.

In a subassembly 500 having a usable or working length of 105 cm, the length 512 of the proximal first layer of adhesive 502 can be about 93-cm, ranging from about 80-cm to about 100-cm. In a subassembly having a usable length of 115 cm, the length 512 of the proximal first layer of adhesive 502 can be about 103-cm, ranging from about 90-cm to about 110-cm. The length 514 of the first distal layer of adhesive 504 can range from about 10 to about 25-cm with a range of about 15 to about 10-cm and a more preferred value of about 17-cm.

FIG. 5 illustrates a side view of an aspiration guide catheter subassembly 600 that comprises a plurality of second layers of adhesive proximal 602, intermediate 604, and distal 606, a proximal outer layer of polymeric coating 608, and a distal layer of outer polymeric coating 624. The subassembly 600 further comprises at least one radiopaque marker band 610 and a transition ring of UV adhesive 618. The proximal second layer of adhesive 602 has a length 612 while the distal second layer of adhesive 606 has a length 616 and the intermediate second layer of adhesive 604 has a length 614. The catheter subassembly 600 further comprises an overlap region 620 disposed at the transition between the proximal second layer of adhesive and the intermediate second layer of adhesive 604. The subassembly 600 further comprises an outer layer of polymeric shrink wrap tubing 622 in the intermediate region.

Referring to FIG. 5, the distal second layer of adhesive 606 is disposed over the distal part of the catheter subassembly 600 as well as being disposed over the intermediate second layer of adhesive 604.

The proximal second layer of adhesive can have a length of about 91-cm (range about 80-cm to about 100-cm) for a catheter having a 105-cm working length and about 101-cm (range about 90-cm to about 110-cm) for a catheter having a 115-cm working length. The length of the intermediate second layer of elastomeric adhesive can be about 5.5-cm with a range of about 3-cm to about 7-cm. The length of the distal layer of elastomeric adhesive can range between about 15-cm and 25-cm with an exemplary value of about 19.5-cm for catheters having working lengths of about 105-cm to about 115-cm. The overlap region 620 can have a length of about 0.5-cm with a range of about 0.1-cm to about 1.0-cm. The length of the UV curable adhesive ring 618 can range from about 0.5-mm to about 2-mm with an exemplary value of about 1.0-mm.

In an embodiment, the radiopaque marker band 610 can be fabricated from platinum iridium wire having a diameter of about 0.002 inches. Materials comprised by the radiopaque marker 610 can include platinum, platinum-iridium, gold, tantalum, barium sulfate, bismuth sulfate, and the like. The radiopaque marker 610 can comprise or be configured as a coil of round wire or flat wire, or it can be configured as an axially elongate cylindrical band, as a serpentine band of wire, or the like. The radiopaque marker 610 can comprise a length of about 0.5 mm to about 5-mm. The radiopaque marker 610 can be embedded within the elastomeric adhesives and be disposed between the innermost layer 304 and the outermost layer of polymer 608 and 624.

The outermost layers of polymer 608, 622, and 624 can be fabricated from materials such as, but not limited to, polyester (PET), polyimide, Pebax™, polyamide, or the like. In some embodiments, the outermost layers of polymer 608 in the proximal region can be configured as heat shrink tubing having a thickness of about 0.001 inches. The outermost layer of polymer 624 in the distal region can comprise polyimide (Pebax™) heat shrink tubing having a thickness of between about 0.0005 and 0.002 inches. The distal outer second polymer layer can be sourced from Iridium corporation. The intermediate outer layer of polymer 622 can comprise polyester (PET) having a wall thickness of about 0.00025 inches, with a range of about 0.0001 to about 0.001 inches.

The second layer of adhesive in the proximal region 602 may comprise Flexobond 431 but can also comprise other similar materials, such as but not limited to other 2-part urethane adhesives, 1-part urethane adhesive, or the like. The second layer of adhesive in the intermediate region 604 comprises Flexobond 430 but can also comprise other similar materials, such as but not limited to other 2-part urethane adhesives, 1-part urethane adhesive, or the like. The second layer of adhesive in the distal region 606 may comprise Flexobond 430 soft mix but other similar materials can also be used.

Figure 6:
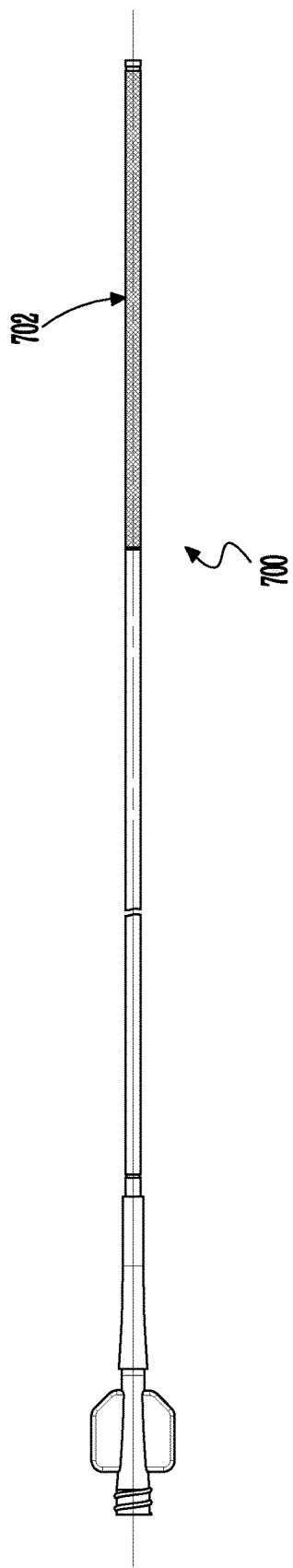
FIG. 6 illustrates a side view of a coated catheter.

FIG. 6 illustrates a side view of an aspiration guide catheter subassembly 700. In catheter subassembly 700 an additional coating layer 702 may be applied to the distal end of catheter. Coating layer 702 may include coating base, a crosslinker A coating, and/or crosslinker B coating.

Figure 7:
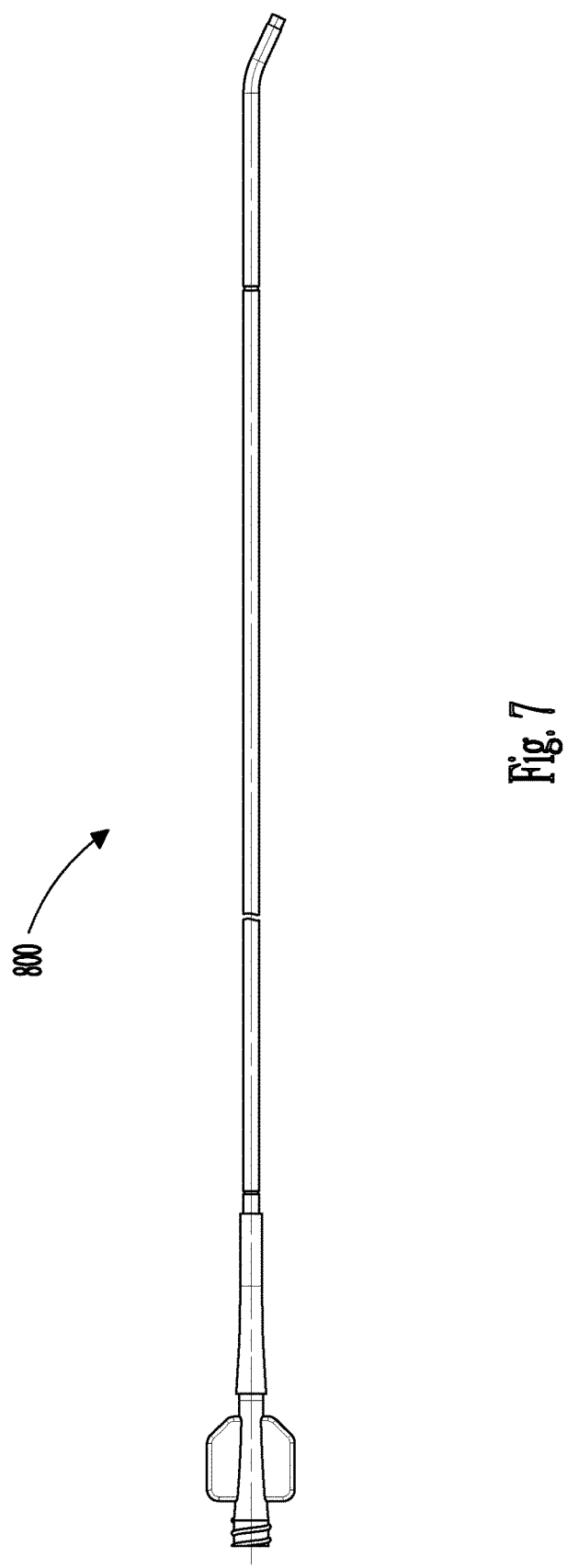
FIG. 7 illustrates a side view of a catheter according to another embodiment of the present disclosure.

FIG. 7 illustrates a guide catheter 800 according to another embodiment of the present disclosure. In this example, guide catheter 800 is similar to guide catheter 100 described above. Whereas guide catheter 100 has a straight configuration, guide catheter 800 has a modified J shape configuration.

In some embodiments of the disclosure, an optional balloon, such as a compliant balloon formed of material such as latex, silicone, polyurethane, C-Flex™ thermoplastic elastomer, Chronoprene™, Santoprene™ or the like, may be positioned at or near the distal end of the elongate catheter body. Such optional balloon may be useful for occluding flow through the blood vessel in which the catheter is positioned when such flow occlusion is desired.

In at least some embodiments, the proximal section 101 will retain radial strength but provide lateral flexibility. Additionally, that section desirably has a lateral flexibility (stiffness), such as would be measured by, for example, a Tinius-Olsen™ Stiffness Tester, of at least 1,200 degrees of deflection/inch-pound (measured at 20 degrees to 30 degrees of deflection, with a 0.005 lb load, over a 0.25" span), preferably 2,500 degrees of deflection/inch-pound. The radial compression strength of the section is quite high as compared to other distal sections found on comparable catheter distal sections of prior art guide catheters.

Access for the catheter of the present disclosure can be achieved using conventional techniques through an incision on a peripheral artery, such as right femoral artery, left femoral artery, right radial artery, left radial artery, right brachial artery, left brachial artery, right axillary artery, left axillary artery, right subclavian artery, or left subclavian artery. An incision can also be made on right carotid artery or left carotid artery in emergency situations.

The construction disclosed herein is suitable for guide catheter as a stand-alone device. This construction results in a highly flexible device having high column strength, torqueability, superior kink-resistance unachievable in prior art devices having a thin wall tube of this size, and high tensile strength.

It is to be appreciated that the disclosure has been described hereabove with reference to certain examples or embodiments of the disclosure but that various additions, deletions, alterations and modifications may be made to those examples and embodiments without departing from the intended spirit and scope of the disclosure. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

The invention claimed is:

1. A catheter device comprising: a catheter body comprising: a tubular member having a lumen and an outer surface, the tubular member comprising a coil defining a plurality of winds separated by gaps and a polymeric material disposed within the gaps, wherein the coil includes a proximal coil portion and a distal coil portion, the distal coil portion being positioned between the proximal coil portion and a distal end of the catheter body, the gaps in the distal coil portion each having a width between about 0.006 inches and about 0.010 inches, and the gaps in the proximal coil portion each having a width between about 0.0005 inches and about 0.002 inches; an inner liner extending through the lumen of the tubular member and defining an inner lumen of the catheter body; and an outer covering on the outer surface of the tubular member, wherein the polymeric material disposed within the gaps comprises a proximal polymeric material portion and a distal polymeric material portion, the distal polymeric material portion being positioned between the proximal polymeric material portion and the distal end of the catheter body, wherein the proximal polymeric material portion is stiffer than the distal polymeric material portion, and wherein the polymeric material disposed within the gaps is different from the materials of the inner liner and outer covering, and wherein a distal region of the catheter body has an inner diameter to wall thickness ratio greater than or equal to 16:1; and a hydrophilic coating on an outer surface of the outer covering.

2. The catheter device according to claim 1 wherein the coil comprises a nickel titanium alloy.

3. The catheter device according to claim 1 wherein the coil is a metal helix.

4. The catheter device according to claim 1 wherein the polymeric material comprises an elastomer.

5. The catheter device according to claim 1 wherein the inner liner comprises at least one material selected from the group consisting of: fluoropolymers; polytetrafluoroethylene (PTFE); perfluoroalkoxy (PFA); and fluorinated ethylene propylene (FEP).

6. The catheter device according to claim 1 wherein the outer covering comprises at least one material selected from the group consisting of: polyesters and polyolefins.

7. The catheter device according to claim 1 wherein the catheter body further has a proximal region and a medial region, the outer covering on the proximal region comprises polyester having a thickness of about 0.001 inch, the outer covering on the medial region comprises polyester having a thickness of about 0.0005 inch, and the outer covering on the distal region comprises polyolefin having a thickness of about 0.0005 inch.

8. The catheter device according to claim 1 wherein the catheter body further has a proximal region and a medial region, wherein the distal region has a lateral flexibility of greater than 1200 degrees of deflection per inch-pound force.

9. The catheter device according to claim 1 wherein the distal region has a kink radius of about 0.174 inch +/−0.008 inch or less.

10. The catheter device according to claim 1 wherein the polymeric material disposed within the gaps is a thermoset polymer.

11. The catheter device according to claim 1 wherein the gaps in the proximal coil portion each have a width of about 0.001 inches and the gaps in the distal coil portion each have a width of about 0.008 inches.

12. The catheter device according to claim 1 wherein the coil is formed from a wire having a thickness of about 0.0005 inches to about 0.005 inches.

13. The catheter device according to claim 1 wherein coil is formed from a wire having a width of about 0.001 inches to about 0.010 inches.

14. The catheter device according to claim 1 wherein the inner liner has an etched exterior surface.

15. The catheter device according to claim 1 wherein the inner diameter to wall thickness ratio of the distal region of the catheter body is between about 16:1 and about 24:1.

16. The catheter device according to claim 1 wherein the polymeric material comprises a cast polyurethane.

17. The catheter device according to claim 16 wherein the cast polyurethane comprises a thermoset polyurethane adhesive.

18. The catheter device according to claim 1 wherein the coil further includes a medial coil portion, the gaps in the medial coil portion each having a width between about 0.002 inches and about 0.006 inches.

19. The catheter device according to claim 18 wherein the gaps in the medial coil portion each have a width of about 0.004 inches.

20. A guide catheter section comprising: an elongate tubular catheter body having a proximal end and a distal end and a passageway defining an inner lumen extending between those ends, the elongate tubular catheter body comprising an inner tubular liner of a first liner material in coaxial relationship with an outer tubular cover and a tubular member between the inner liner and outer cover, the tubular member comprising a metallic coil structure defining metallic winds and a polymeric kink resistance member filling the gap within the metallic winds, wherein the polymeric kink resistance member comprises a proximal adhesive portion and a distal adhesive portion, the distal adhesive portion being positioned between the proximal adhesive portion and the distal end of the catheter body, wherein the proximal adhesive portion is stiffer than the distal adhesive portion, the catheter section, in the region of the distal end, having an inner diameter to wall thickness ratio in greater than or equal to 16:1 and a kink radius of about 0.174 inch +/−0.008 inch or less, wherein the inner liner has an etched exterior surface, wherein the metallic coil structure includes a proximal coil portion and a distal coil portion, the distal coil portion being positioned between the proximal coil portion and the distal end of the catheter body, the gaps in the distal portion each having a width between about 0.006 inches and about 0.010 inches, and the gaps in the proximal coil portion each having a width between about 0.0005 inches and about 0.002 inches.

21. A method comprising: inserting into a subject's vasculature a catheter device comprising: a catheter body comprising: a tubular member having a lumen and an outer surface, the tubular member comprising a coil defining a plurality of winds separated by gaps and a polymeric material disposed within the gaps, wherein the coil includes a proximal coil portion and a distal coil portion, the distal coil portion being positioned between the proximal coil portion and a distal end of the tubular member, the gaps in the distal coil portion each having a width between about 0.006 inches and about 0.010 inches, and the gaps in the proximal coil portion each having a width between about 0.0005 inches and about 0.002 inches; an inner liner extending through the lumen of the tubular member and defining an inner lumen of the catheter body; an outer covering on the outer surface of the tubular member; and a hydrophilic coating on an outer surface of the outer covering, wherein the polymeric material disposed within the gaps comprises a proximal polymeric material portion and a distal polymeric material portion, the distal polymeric material portion being positioned between the proximal polymeric material portion and the distal end of the catheter body, wherein the proximal polymeric material portion is stiffer than the distal polymeric material portion, and wherein the polymeric material disposed within the gaps is different from the materials of the inner liner and the outer covering, and wherein a distal region of the catheter body has an inner diameter to wall thickness ratio greater than or equal to 16:1; and delivering a substance or device through the inner lumen of the catheter device.

22. The method according to claim 21 wherein inserting the catheter device comprises advancing the catheter device into a blood vessel located within the subject's skull.

23. The method according to claim 22 wherein the blood vessel into which the catheter device is advanced is selected from the group consisting of: carotid artery, cerebral artery, anterior cerebral artery, middle cerebral artery and posterior cerebral artery.

24. A method comprising: forming a catheter body, wherein forming the catheter body comprises: forming or obtaining a coil defining a plurality of winds separated by gaps, wherein the coil includes a proximal coil portion and a distal coil portion, the distal coil portion being positioned between the proximal coil portion and a distal end of the catheter body, the gaps in the distal coil portion each having a width between about 0.006 inches and about 0.010 inches, and the gaps in the proximal coil portion each having a width between about 0.0005 inches and about 0.002 inches; disposing polymeric material within the gaps such that the polymeric material and the coil, in combination, form a tubular member having an outer surface and a lumen, wherein the polymeric material disposed within the gaps comprises a proximal polymeric material portion and a distal polymeric material portion, the distal polymeric material portion being positioned between the proximal polymeric material portion and the distal end of the catheter body, wherein the proximal polymeric material portion is stiffer than the distal polymeric material portion; and disposing an inner liner within the lumen of the tubular member, the inner liner defining an inner lumen; and disposing an outer covering on the outer surface of the tubular member, wherein the polymeric material disposed within the gaps is different from the materials of the inner liner and the outer covering, and wherein a distal region of the catheter body has an inner diameter to wall thickness ratio greater than or equal to 16:1; and applying a hydrophilic coating to an outer surface of the outer covering.

25. The method according to claim 24 further comprising disposing a radiographic marker on or in the catheter body.

26. The method according to claim 24 wherein the outer covering comprises a tube that initially has an inner diameter that is larger than the outer diameter of the tubular member and wherein disposing the outer covering on the outer surface of the tubular member comprises advancing the outer covering over the tubular member and causing the outer covering to contact the outer surface of the tubular member.

27. The method according to claim 26 further comprising heat shrinking the outer covering onto the outer surface of the tubular member.

28. The method according to claim 24 wherein disposing the inner liner within the lumen of the tubular member comprises disposing the inner liner on a mandrel and positioning the coil on top of the inner liner.

29. The method according to claim 28 wherein the coil comprises a nickel titanium alloy and disposing an inner liner within the lumen of the tubular member comprises helically winding the nickel titanium alloy about the inner liner and then heat setting the nickel titanium alloy.

30. The method according to claim 28 wherein disposing the inner liner within the lumen of the tubular member comprises casting a flowable polymer mixture into the gaps and allowing the flowable polymer mixture to solidify, thereby forming the tubular member with the inner liner disposed therein.

31. The method according to claim 30 wherein the polymeric material comprises a thermoset polymer.

32. The method according to claim 30 wherein the polymeric material comprises a polymer adhesive.

33. The method according to claim 32 further comprising applying a release agent or barrier to one or more selected areas of the coil to deter or interrupt adhesion of the polymer adhesive to the selected areas of the coil.

* * * * *